United States Patent
Fehr et al.

(10) Patent No.: US 8,876,769 B2
(45) Date of Patent: Nov. 4, 2014

(54) MEDICAL INFUSION SYSTEM WITH PULSE WIDTH MODULATION AND SAFETY CIRCUIT

(75) Inventors: Jean-Noël Fehr, Neuchatel (CH); Thomas Von Büren, Bern (CH); Stefan Troller, Sissach (CH); Marc Mattmüller, Wünuewil (CH)

(73) Assignee: Roche Diagnostics International AG, Rotkreuz (CH)

( * ) Notice: Subject to any disclaimer, the term of this patent is extended or adjusted under 35 U.S.C. 154(b) by 1039 days.

(21) Appl. No.: 12/484,335

(22) Filed: Jun. 15, 2009

(65) Prior Publication Data

US 2010/0121277 A1     May 13, 2010

(30) Foreign Application Priority Data

Jun. 20, 2008 (EP) ...................... 08158667

(51) Int. Cl.
- *A61M 5/142* (2006.01)
- *G05B 9/02* (2006.01)
- *H02P 7/29* (2006.01)
- *A61M 5/172* (2006.01)

(52) U.S. Cl.
CPC .............. *A61M 5/142* (2013.01); *A61M 5/172* (2013.01); *A61M 2005/14208* (2013.01); *H02P 7/29* (2013.01)
USPC ............................ 604/151; 318/139; 318/563

(58) Field of Classification Search
USPC .............. 361/160, 194; 417/477.5–9; 429/90; 604/313, 6.11, 131, 151; 318/139, 563
See application file for complete search history.

(56) References Cited

U.S. PATENT DOCUMENTS

| | | | | |
|---|---|---|---|---|
| 4,207,503 A | * | 6/1980 | Irschik et al. | ................. 318/139 |
| 6,074,775 A | * | 6/2000 | Gartstein et al. | ................. 429/53 |
| 6,239,991 B1 | | 5/2001 | Ajro et al. | |
| 8,027,572 B2 | * | 9/2011 | Bedingfield et al. | .......... 392/315 |
| 2002/0071225 A1 | | 6/2002 | Sheldon et al. | |
| 2002/0171297 A1 | * | 11/2002 | Talbot et al. | .................. 307/118 |
| 2003/0014022 A1 | * | 1/2003 | Lockwood et al. | ........... 604/315 |

FOREIGN PATENT DOCUMENTS

WO    03029909 A1    4/2003

OTHER PUBLICATIONS

U. Tietze et al., Halbleiter-Schaltungstechnik, 19000101, vol. 12, 2002, XP009108925, p. 1-8, Germany.
Thomas Sehaerer, Vom Passiven RC-Zum, www.elektronik-kornpendium.de/public/schaerer/rcdhp.htm, Nov. 14, 2008, XP007906389, pp. 1-5.
European Search Report, Appl No. EP 08 15 8667, Nov. 20, 2008.

* cited by examiner

*Primary Examiner* — Quynh-Nhu H Vu
(74) *Attorney, Agent, or Firm* — Dinsmore & Shohl LLP

(57) ABSTRACT

A medical infusion system with pulse width modulation and a safety circuit and a method thereof are disclosed. Embodiments of the system include a switching device and a pump motor, wherein the pump motor and the switching device are connected in series and constitute a power supply circuit to be connected to a power supply. Embodiments of the system further includes a control signal generator configured to generate a control signal e.g. PWM, and which is connected to input of the safety circuit. Output of the safety circuit is connected to a control input of the switching device such that the pump motor will not operate if there is no control signal applied to the input of the safety circuit.

18 Claims, 7 Drawing Sheets

US 8,876,769 B2

MEDICAL INFUSION SYSTEM WITH PULSE WIDTH MODULATION AND SAFETY CIRCUIT

TECHNICAL FIELD

Embodiments of the present invention relate generally to medical infusion systems, and in particular to medical infusion system with pulse width modulation and a safety circuit. comprising a control signal generator, a safety circuit, a switching device and a pump motor. The invention further relates to a method for driving a pump motor in a medical infusion system.

BACKGROUND

Conventional medical infusion systems utilize a variety of motor technologies for driving the infusion pump such as direct current motors, stepper motors, or solenoid motors. When using such a motor in an infusion pump, safety measures must be designed to protect the user from malfunction of the motor, especially to avoid delivering an excessive amount of a substance or drug, for example insulin, to be infused to the user. This might especially occur in case of a short circuit that bypasses the control system of the motor.

United States Patent Application US 2002/0071225 A1 discloses several solutions for this problem. The first solution is using a motor that needs a multiple of the voltage provided by the battery. In case a short circuit directly connects the motor to the battery, the voltage is not sufficient to drive the motor. A second solution uses a safety circuit that closes the power supply circuit of the pump motor only when a special AC signal is applied to the safety circuit.

The drawback of the first solution is that an expensive and complex DC-DC step-up converter is needed. The drawback of the second solution is that a second dedicated circuit is needed next to control electronics that control the rated supply voltage and therefore the motor in order to regulate the amount of substance or drug to be infused.

SUMMARY

It is against that above background that embodiments of the present invention provide an improved and simple device and method for controlled and safe infusion of a substance or drug.

In one embodiment, disclosed is a medical infusion system comprising a control signal generator, a safety circuit, a switching device, and a pump motor. The pump motor and the switching device are connected in series and constitute a power supply circuit to be connected to a power supply. The control signal generator is configured to generate a control signal having an "on" potential and an "off" potential present at a control input of the switching device. The "on" potential is any potential which makes the switching device close the power supply circuit, and the "off" potential is any potential which makes the switching device open the power supply circuit. An output of the control signal generator is connected to an input of the safety circuit. An output of the safety circuit is connected to the control input of the switching device. The safety circuit is configured to apply the "off" potential to its output if there is an "off" potential at its input, apply the "on" potential to its output if there continuously is an "on" potential at its input for a duration up to a predetermined amount of time, and apply the "off" potential to its output if there continuously is an "on" potential at its input for a duration longer than a predetermined amount of time.

In another embodiment, a method for driving a pump motor in a medical infusion system, wherein the pump motor and a switching device constitute a power supply circuit to be connected to a power supply, is disclosed. The method comprises receiving at a control input of the switching device a control signal from a control signal generator with a safety circuit. The control signal includes an "on" potential and an "off" potential, wherein the "on" potential is any potential that makes the switching device close the power supply circuit, and the "off" potential is any potential that makes the switching device open the power supply circuit. The method also includes switching the power supply circuit of the pump motor by the switching device according to the control signal applied to the control input of the switching device; applying the "off" potential to its output if there is the "off" potential at its input; applying the "on" potential to its output if there continuously is the "on" potential at its input for a duration up to a predetermined amount of time; and applying the "off" potential to its output if there continuously is the "on" potential at its input for a duration longer than a predetermined amount of time.

These and other advantages and features of the invention disclosed herein will be made more apparent from the description, drawings and claims that follow.

BRIEF DESCRIPTION OF THE DRAWINGS

A detailed description of embodiments of the invention will be made with reference to the accompanying drawings, wherein like numerals designate corresponding parts in a several figures. Combinations of single features of the several exemplary embodiments are possible.

DETAILED DESCRIPTION

Figure 1:
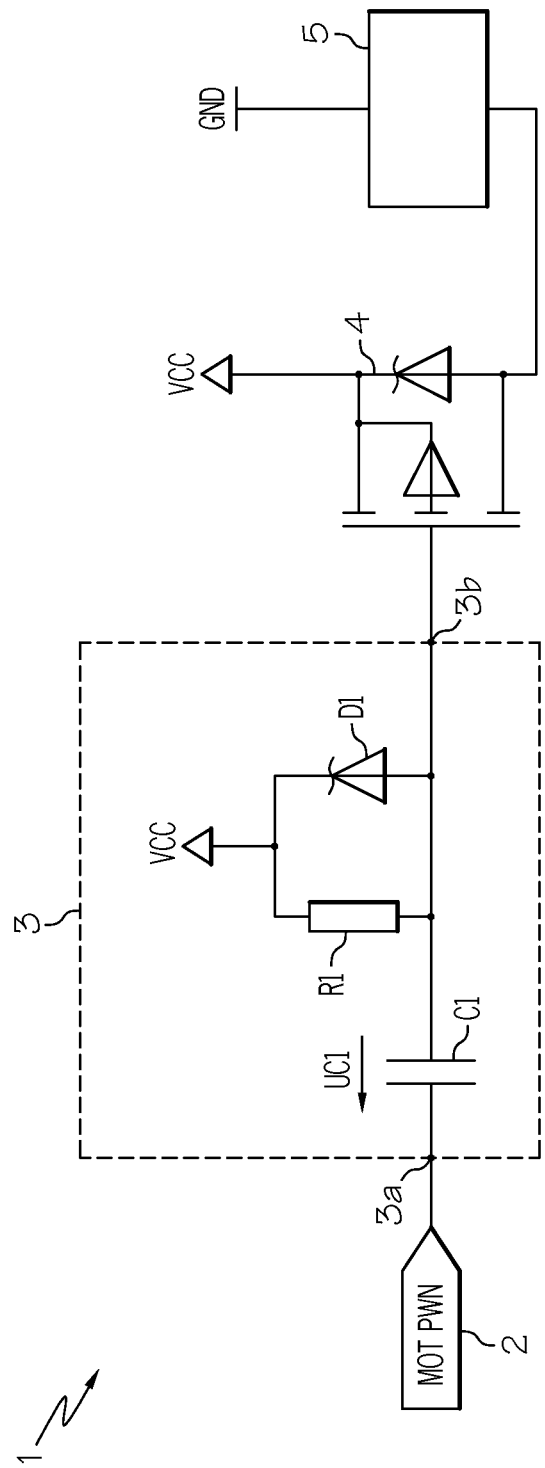
FIG. 1 shows a first embodiment of a medical infusion system.

In one embodiment a medical infusion system is disclosed. The system comprises a control signal generator, a safety circuit, a switching device and a pump motor, wherein the pump motor and the switching device are connected in series and constitute a power supply circuit to be connected to a power supply, the output of the control signal generator is connected to the input of the safety circuit and the output of the safety circuit is connected to a control input of the switching device. The voltage of the power supply is termed VCC.

The pump motor preferably is a DC motor. The pump motor is part of a pump that delivers a substance or drug or the pump motor drives a piston inside a container holding the substance or drug.

The control signal generator is configured to generate a control signal with two potentials, an "on" potential and an "off" potential, wherein an "on" potential is any potential that, if this potential is present at a control input of the switching device, makes the switching device close the power supply circuit, and an "off" potential is any potential that makes the switching device open, that means interrupt, the power supply circuit. Depending on the actual switching device used, the "on" potential can be a constant (positive) voltage, that is logical "high", or ground, that is logical "low".

The safety circuit is configured to apply an "off" potential to its output if there is an "off" potential at its input; to apply an "on" potential to its output if there continuously is an "on" potential at its input for a duration up to a predetermined amount of time; and to apply an "off" potential to its output if there continuously is an "on" potential at its input for a duration longer than a predetermined amount of time.

In operation, the safety circuit receives the control signal from the control signal generator, wherein the control signal has the potentials as described above. The switching device switches the power supply circuit of the pump motor according to the signal applied to the control input of the switching device. This causes operation of the motor and thus infusion of a substance or drug controlled by the control signal. The motor control is very exact, resulting in a highly accurate delivery rate. In addition, surge currents are reduced which increases battery life.

The safety circuit applies an "off" potential to its output if there is an "off" potential at its input; applies an "on" potential to its output if there continuously is an "on" potential at its input for a duration up to a predetermined amount of time; and applies an "off" potential to its output if there continuously is an "on" potential at its input for a duration longer than a predetermined amount of time.

This means that the safety circuit applies a potential to its output that is equivalent to the potential it has at its input. An exception to this is when the signal at its input has "on" potential for a duration longer than a predetermined amount of time. This is a situation that could mean an overdose to the patient. In this case, the safety circuit applies an "off" potential to its output even though it has an "on" potential at its input. Thus, a signal to interrupt the power supply circuit is devised from the control signal, which controls the motor and for this reason the delivery rate, itself.

Depending on the structure of the safety circuit, the signal at the output of the safety circuit might be (slightly) delayed compared to the signal at the input of the safety circuit. This does not affect the function of the medical infusion system, especially if the control signal has a high frequency.

In a preferred embodiment, the control signal generator is a signal generator configured to generate a pulse width modulation (PWM) signal. The received control signal then is a PWM signal. A PWM signal is a square wave signal with a fixed frequency. Within one cycle, the amplitude of the PWM signal changes twice, first from high to low and then from low to high or via versa.

The high amplitude usually is any positive DC voltage, for example 3V or 5V, while the low amplitude usually is zero or ground. The duty cycle of a PWM signal denotes the fraction of time the signal is high during a cycle.

The medical infusion system and method described so far fulfil two tasks. The first task is to modulate/switch the power supply circuit on and off according to the control signal, thus allowing to control the amount of substance or drug to be infused to the user. The second task is to interrupt the power supply circuit, which means turning off the motor, if the motor was operating continuously for a predetermined amount of time. This means that the amount of substance or drug to be infused to the user at a time can be limited to a none live-threatening dose. In a preferred embodiment, the predetermined amount of time is much longer than the cycle of the PWM signal, for example more than 40 times the PWM cycle.

This means that the safety circuit does not engage, that is interrupts the power supply circuit, before a PWM cycle is over.

In a further preferred embodiment of the present invention, the safety circuit, the switching device and the pump motor constitute a unit that is impervious to fluid, for example by a liquid-tight sealing. This means that fluids, especially the substance or drug to be infused, can't penetrate into the unit to cause failures like e.g. a short circuit.

Since the safety circuit eliminates the effect of a short circuit that occurs between the control signal generator and the switching device, and a short circuit can't occur within the liquid-tight sealing, the best possible protection of the user against malfunctions of the medical infusion system is provided.

According to a special embodiment of the invention, the safety circuit comprises an RC circuit. Preferably, one pin of the capacitor of the RC circuit is directly connected to the input of the safety circuit, the other pin of the capacitor is directly connected to the output of the safety circuit, one pin of the resistor of the RC circuit is directly connected to the output of the safety circuit and the other pin of the resistor is connected to a constant potential being equal to the "off" potential.

While the signal received by the safety circuit, the input signal, has "on" potential, the capacitor of the RC circuit is charged via the resistor of the RC circuit. The potential at the pin of the capacitor that is connected to the resistor is applied to the control input of the switching device. This potential changes towards the "off" potential with a rate following an exponential function determined by the time constant R*C. If this potential has reached a certain level, the switching device will interrupt the power supply circuit. This level, the switching threshold (termed VST), depends on the switching device.

As a preferred option, the safety circuit comprises a diode in parallel to the resistor of the RC circuit so that the capacitor of the RC circuit is discharged via the diode if the signal at the input of the safety circuit has "off" potential, that is if the received signal causes the switching device to interrupt the power supply circuit. This enables rapid discharging of the capacitor which is necessary to reset the safety circuit so that the switching device can close the power supply circuit the next time an "on" potential is applied to the input of the safety circuit. Otherwise the capacitor would be discharged only via the resistor, which would be too slow due to the time constant of the RC circuit. If the capacitor wasn't sufficiently discharged when the input signal changes from "off" to "on" potential, the remaining voltage over the capacitor would prevent the switching device from closing the power supply circuit.

The switching device can be of any kind, for example an electro-mechanical switch like a relay or a transistor, like an FET or MOSFET. The only limitation is that the switching device must be fast enough to follow the control signal.

In one embodiment, the switching device is a PMOSFET (a p-channel MOSFET), the "on" potential is ground and the "off" potential is a constant positive potential (VPOS). This constellation is used if the switching device is placed between the pump motor and the positive pole of the power supply. In this embodiment, the PMOSFET conducts if the potential at its gate is below VST, which is low. That means that the PMOSFET closes the power supply circuit if the control signal applied to the safety circuit is low. In this case, the capacitor is charged via the resistor and the potential at its pin that is connected to the output of the safety circuit rises towards VPOS. The PMOSFET opens, which means interrupts, the power supply circuit when charging of the capacitor has reached a certain level, which is the switching threshold VST of the switching device.

In another embodiment, the switching device is an NMOSFET (an n-channel MOSFET), the "on" potential is a constant positive potential (VPOS) and the "off" potential is ground. This embodiment is complementary to the previous embodiment and is useful if the switching device is located between the motor and the negative pole of the power supply or ground. In this embodiment, the NMOSFET conducts if the potential at its gate pin is higher than VST, that is high. In this case, the capacitor is charged via the resistor and the potential at its pin that is connected to the output of the safety circuit falls towards ground. The NMOSFET opens, which means interrupts, the power supply circuit when charging of the capacitor has reached a certain level that is the switching threshold VST of the NMOSFET. To achieve the same amount of substance or drug to be infused, the control signal has to be the inverse of the control signal of the previous embodiment.

In a preferred embodiment, the constant positive potential VPOS equals the voltage VCC of the power supply. This means that only one voltage is present in the medical infusion system and, in the embodiment using the PMOSFET or any other switching device that opens (interrupts) its output while the signal at its input exceeds a positive switching threshold, the resistor of the RC circuit can be connected to the positive pole of the power supply.

The safety circuit of the medical infusion system according to the present invention prevents the pump motor from being supplied with current if the duty cycle of the PWM signal at the input of the safety circuit is outside of special boundaries, for example smaller than 2% or larger than 98%.

It is apparent to the person skilled in the art that additional switching devices can be provided in the power supply circuit to stop the motor if certain conditions are met.

In the following illustrated embodiments, all potentials are given with relation to ground. Potentials are also described by their logical counterparts, where zero or ground is logical low and a positive voltage larger than a threshold, for example the switching threshold of a switching device, is logical high. Directly connected means that there is no other component, like for example a diode or a capacitor, between the elements, except for a conductor. This means that nothing but a conductor is between a pin of the first element and a pin of the second element.

FIG. 1 shows a medical infusion system 1 with a control signal generator 2, a safety circuit 3, a PMOSFET 4 as a switching device and a DC pump motor 5. The output of the control signal generator 2 is connected to an input 3a of the safety circuit 3, the output 3b of the safety circuit 3 is connected to the gate of the PMOSFET 4, which is the control input of the switching device. The pump motor 5 is connected to a power supply (not shown) with a ground pole (GND) and a positive pole having a voltage VCC versus ground. The PMOSFET 4, for example an IRF5851, is included in the power supply circuit between the pump motor 5 and the positive pole of the power supply with its source and drain pins.

The safety circuit 3 comprises an RC circuit with the capacitor C1 and the resistor R1. One pin of the capacitor C1 is directly connected to the input 3a, the other pin of the capacitor C1 is directly connected to the output 3b of the safety circuit 3. One pin of the resistor R1 is directly connected to the output 3b, the other pin of the resistor R1 is directly connected to the positive pole of the power supply. In parallel to the resistor R1 is a diode D1, for example a PMEG2005AEA, with its cathode pointing towards the positive pole of the power supply.

Operation of the medical infusion system 1 is described starting with an uncharged capacitor C1. The signal generator 2 generates a PWM signal with the two amplitudes 0 (ground, GND, logical low) and VCC (logical high).

If the PWM signal at the input 3a changes to high, the potential at output 3b changes to high (that means VCC), too, because capacitor C1 is uncharged. Due to the potentials in the safety circuit 3, the capacitor C1 is not being charged. The high potential of the output 3b is applied to the gate of PMOSFET 4 that therefore opens the power supply circuit and there is no current through the pump motor 5. This means that, in this embodiment, VCC (or logical high) corresponds to the "off" potential, while ground (or logical low) is the "on" potential.

If the PWM signal at the input 3a changes from high to low, the potential at the output 3b also changes to low due to the still uncharged capacitor C1. Therefore the PMOSFET 4 closes the power supply circuit and current flows through the pump motor 5. Due to the potential difference between VCC at the resistor R1 and ground at input 3a, a current flows through resistor R1 that charges capacitor C1. The voltage UC1 over the capacitor C1 (voltage from 3a to 3b) increases following an exponential rise determined by the time constant τ=R1*C1, see FIG. 5.

If there is no malfunction, the PWM signal returns back from low ("on" potential) to high ("off" potential) before the voltage UC1 has reached the switching threshold VST of PMOSFET 4, that means a value that causes PMOSFET 4 to open the power supply circuit. If the signal at input 3a gets high, which means VCC, the potential at output 3b tends to change to VCC+UC1, which causes PMOSFET 4 to open the power supply circuit. Since the potential at output 3b is larger than VCC, capacitor C1 is discharged via resistor R1. As long as the voltage UC1 is larger than the forward voltage VD1 of diode D1, the diode D1 is in the conducting state and rapidly discharges capacitor C1 to UC1=0 in addition to resistor R1.

If the PWM signal at input 3a does not return to high, the capacitor C1 keeps charging asymptotically to UC1=VCC. If UC1, and thus the potential at output 3b, has reached the switching threshold VST of PMOSFET 4, the PMOSFET 4 opens the power supply circuit and interrupts the flow of current through pump motor 5. When the PWM signal at input 3a returns to high, the capacitor C1 is discharged via resistor R1 and, depending on the voltage UC1, via diode D1, resulting in potential VCC at output 3b which still causes PMOSFET 4 to interrupt the power supply circuit.

If diode D1 wasn't present, discharging of capacitor C1 if the PWM signal at input 3a of the safety circuit 3 turns to high would only happen through resistor R1. Due to the time constant of the RC circuit, the capacitor C1 might not be discharged before the PWM signal at input 3a returns to low, thus unintentionally preventing PMOSFET 4 to close the power supply circuit.

In the medical infusion system 1, preferably the safety circuit 3, the PMOSFET 4 and the pump motor 5 are encapsulated to a liquid-tight unit. This unit has only three electric ports, two for connecting the unit to a power supply and one for connecting the unit to the signal generator 2. Optionally, the signal generator 2, too, can be included in the liquid-tight unit. The unit then has just the two electric ports to be connected to the power supply. Optionally, the whole electronic, too, can be included in the liquid-tight unit.

The time at which a capacitor in an RC circuit is considered to be fully charged is usually calculated as T=5*τ. If T, which is the maximum time the power supply circuit shall be closed, is chosen to be 25 ms and R1 is chosen to be 50 kΩ, the equation τ=R1*C1 leads to C1=100 nF. If the PWM frequency is 3.2 kHz, T is 80 times the duration of a PWM cycle. Other values for the components could be R1=22 kΩ and C1=10 µf, resulting in T=1.1 s.

The minimal PWM frequency is mainly determined by the motor characteristics. Based on the motor parameters, the time T can be defined considering the following dimensioning rules: (A) the RC circuit has to fulfil its functionality, and (B) the time T has to be as small as possible to prevent undesired infusion and needs to be small enough to prevent an excessive delivery of insulin.

The switching circuit, PMOSFET 4, switches from "off" to "on" states at a defined voltage VST. For a PMOSFET, VST is VCC—Vthreshold. Vthreshold is mainly defined by the PMOSFET electrical characteristics and in this embodiment supposed to be much smaller than VCC. Typical values for Vthreshold are: 0.3 V to 0.7 V, typical values for VCC are 3V to 5V.

The functionality of the safety circuit is to allow a PWM signal to flow through the motor, and hence is to transmit the signal generated by the signal generator 2 basically unchanged from input 3a to output 3b if the signal is correct and to block the signal if it is not correct (in state "on" for a time longer than T).

Figure 5:
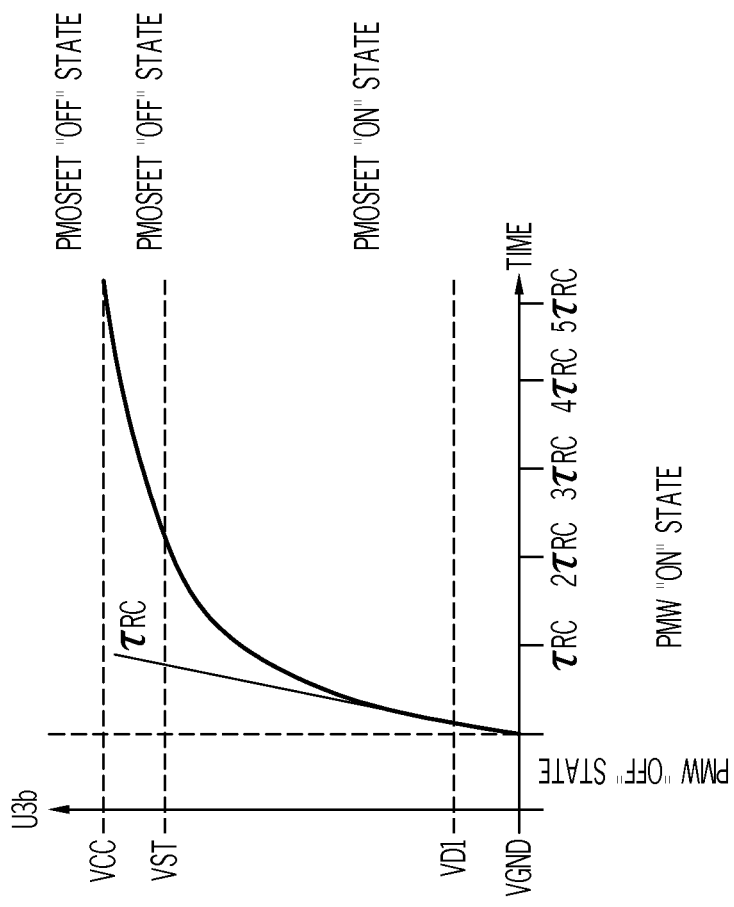
FIG. 5 shows the potential at the output of the safety circuit over time.

The PWM signal is transferred unchanged from input 3a to output 3b if the safety circuit does not block the PWM signal. In the embodiment of FIG. 5, the PWM "on" state time has to be shorter than 2 τRC. Typically τRC is chosen such that 1/τRC<PWM frequency.

Figure 6:
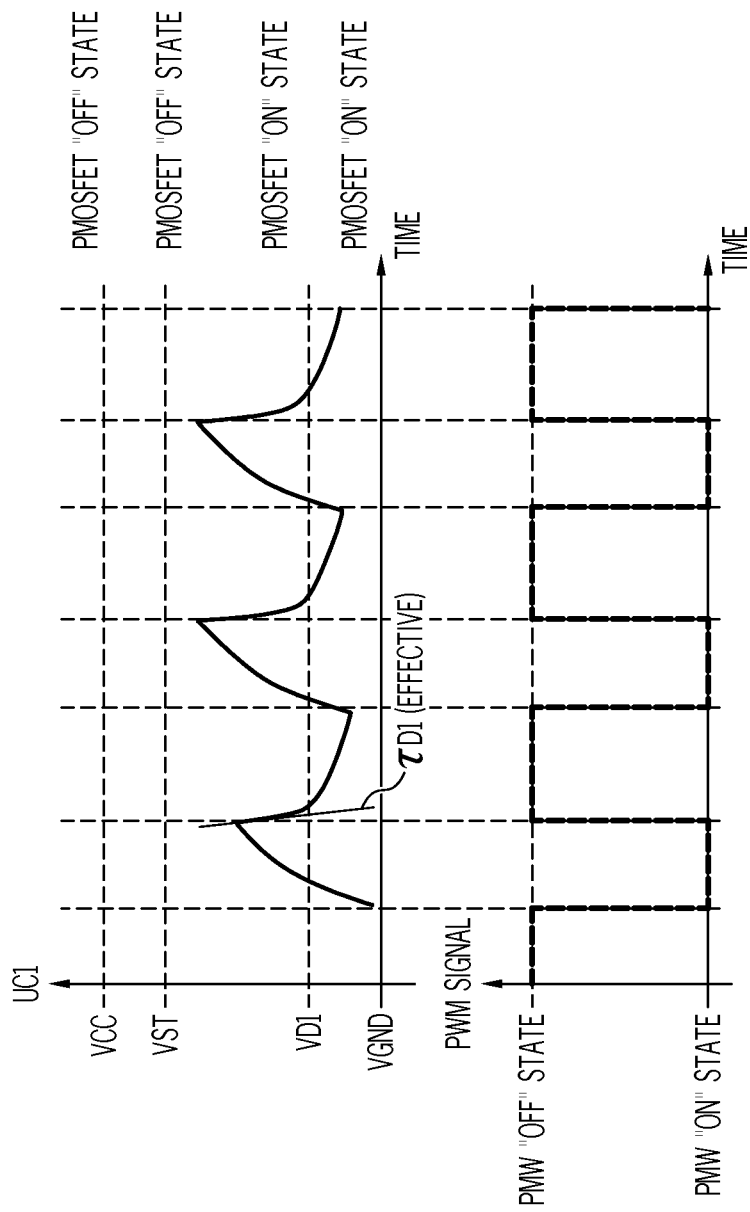
FIG. 6 shows the potential over the capacitor of the safety circuit over time.

Another condition to transfer the signal unchanged is that the capacitor C1 discharge over the diode D1 is sufficient to guarantee that by the next charging of the capacitor C1, the voltage UC1 stays under VST as in FIG. 6.

Figure 7:
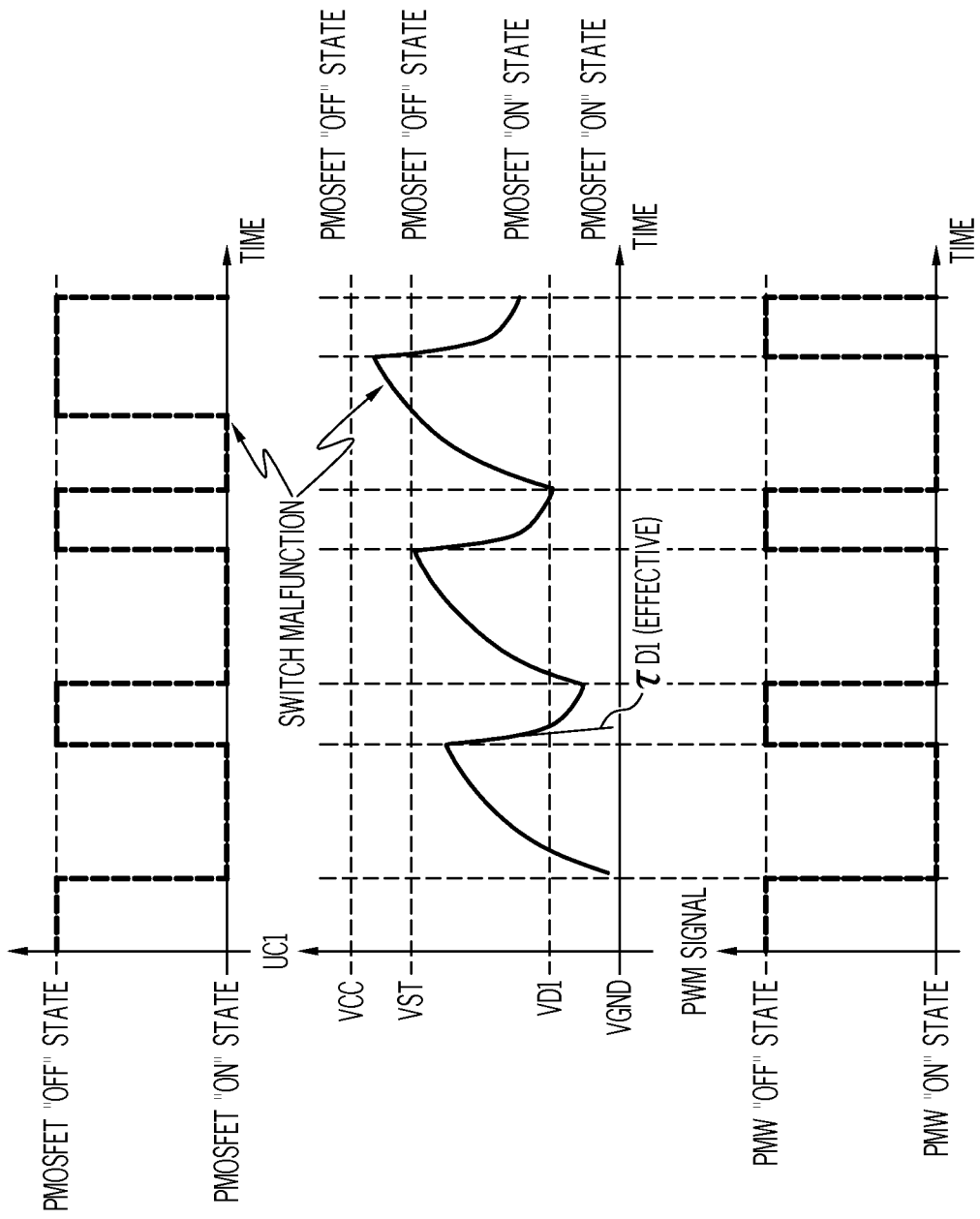
FIG. 7 shows the potential over the capacitor of the safety circuit over time in case of a malfunction.

If discharge of the capacitor C1 over the diode is not sufficient to guarantee that by the next charging of the capacitor C1 the voltage UC1 stays under VST=VCC−Vthreshold, the PWM signal will be changed by the safety circuit as in FIG. 7. In the embodiment of FIG. 7, the duty cycle is 80%.

As the discharge of C1 over the diode D1 is not instantaneous, the PWM duty cycle at the output 3b of the safety circuit 3 may get smaller than the duty cycle at the output 3a of the safety circuit 3, which leads to change of the PWM signal through the safety circuit 3. This is shown in the middle graph of FIG. 7. In each cycle, a little more potential remains in the capacitor C1 if discharging is not fast enough. This remaining potential may sum up over several PWM cycles so that VST is erroneously reached, thus blocking the PWM signal. This means that the safety circuit 3 transforms the PWM signal at its input 3a, shown in the lower graph of FIG. 7, into a different PWM signal at its output 3b, shown in the upper graph of FIG. 7.

This means that the maximal duty cycle that can be applied to the input 3a of the safety circuit 3 without modifying and in worst case permanently blocking the PWM signal by the safety circuit 3 is limited. For the implementation of a safety circuit 3, the components R1, D1 and C1 are preferably chosen such that the maximal duty cycle is larger than 90% and particularly larger than 98%.

For a defined safety circuit (D1, R1, C1), the discharge of the capacitor over the diode D1 can be characterised by a τD1(effective). So a condition for the safety circuit is τD1 (effective)<<τRC. A limitation for the PWM "off" time is that PWM "off" time>5/τD1(effective).

The second design rule implies that the time T is as short as possible. To ensure the safety circuit functionality, the time T should be not smaller than 5 τRC. The time T is also designed to prevent an excessive delivery of insulin. The maximal time T is a function of the delivery flow speed and is much bigger than 5 τRC. It can be defined by the insulin overdose delivered to the patient before the motor is stopped. The insulin overdoses must not have health consequences for the patient. T would preferably be defined such that the insulin overdose during the time T is smaller than 10% to 20% of the daily insulin dose.

Figure 2:
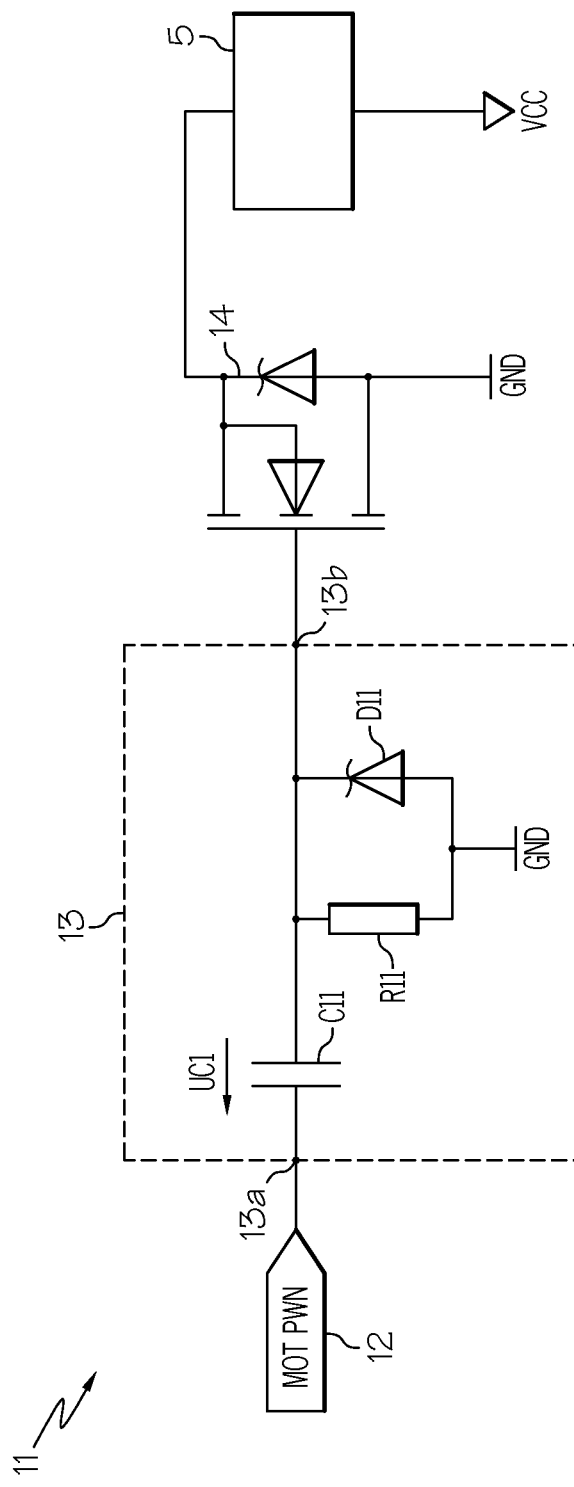
FIG. 2 shows a second embodiment of a medical infusion system.

FIG. 2 shows a complementary embodiment of the one shown in FIG. 1. The switching device of the medical infusion system 11 is placed in the power supply circuit between the pump motor 5 and the ground pole (GND) of the power supply (not shown) with its source and drain pins. With this configuration, the switching device is an NMOSFET (n-channel MOSFET) 14, for example an IRF5851. The gate of the NMOSFET 14 is connected to an output 13b of a safety circuit 13. An input 13a of the safety circuit 13 is connected to the output of a PWM signal generator 12. The NMOSFET 14 closes the power supply circuit if it has a high signal at its gate.

The safety circuit 13 comprises a capacitor C11, a resistor R11 and a diode D11. One pin of the capacitor C11 is directly connected to input 13a, the other pin of the capacitor C11 is directly connected to output 13b. One pin of resistor R11 is directly connected to output 13b, which means that it is directly connected to one pin of capacitor C11, the other pin of the resistor R11 is directly connected to ground potential. The diode D11 is placed in parallel to the resistor R11 with its cathode pointing towards output 13b.

If capacitor C11 is uncharged, that is UC1=0, and PWM signal generator 12 delivers a low signal to input 13a of the safety circuit 13, the potential at output 13b is low and NMOSFET 14 interrupts the power supply circuit. This means that, in this embodiment, ground (or logical low) is the "off" potential while VCC (or logical high) is the "on" potential.

If the amplitude of the PWM signal at input 13a changes to high, for example the voltage VCC of the power supply, the potential at output 13b changes to high and the NMOSFET 14 closes the power supply circuit. At the same time, charging of capacitor C11 starts via resistor R11 with a rate depending on the time constant R11*C11. The voltage UC1 falls following an exponential function with an asymptotical value of −VCC. At the same time the potential at output 13b falls following an exponential function from VCC to 0. If the signal at input 13a is high for longer than a certain amount of time depending on the values of the capacitor C11 and the resistor R11, the potential at output 13b falls below the switching threshold VST of NMOSFET 14, that is to a level that makes NMOSFET 14 interrupt the power supply circuit. In this embodiment, VST equals Vthreshold of the NMOSFET 14.

If the amplitude of the PWM signal at input 13a changes to low, the potential at output 13b tends to change to the voltage UC1 which is negative, and thus NMOSFET 14 opens the power supply circuit. The capacitor C11 is discharged via resistor R11 and in addition via diode D11 while the absolute value of UC1 exceeds the forward voltage of diode D11. After discharging, voltage UC1 and therefore the potential at output 13b is zero and NMOSFET 14 still interrupts the power supply circuit.

Dimensioning of the components of safety circuit 13 is analogous to the medical infusion system 1 according to FIG. 1, which means the resistor R11 is chosen to 50 kΩ and the capacitor C11 is calculated to 100 nF to achieve a time T=25 ms which is the maximum time that NMOSFET 14 closes the power supply circuit. Other values for the components could be R1=22 kΩ and C1=10 µf, resulting in T=1.1 s.

In the medical infusion system 11, preferably the safety circuit 13, the NMOSFET 14 and the pump motor 5 are encapsulated to a liquid-tight unit. This unit has only three electric ports, two for connecting the unit to a power supply and one for connecting the unit to the signal generator 2. Optionally, the signal generator 2, too, can be included in the liquid-tight unit. The unit then has just the two electric ports to be connected to the power supply.

Figure 3:
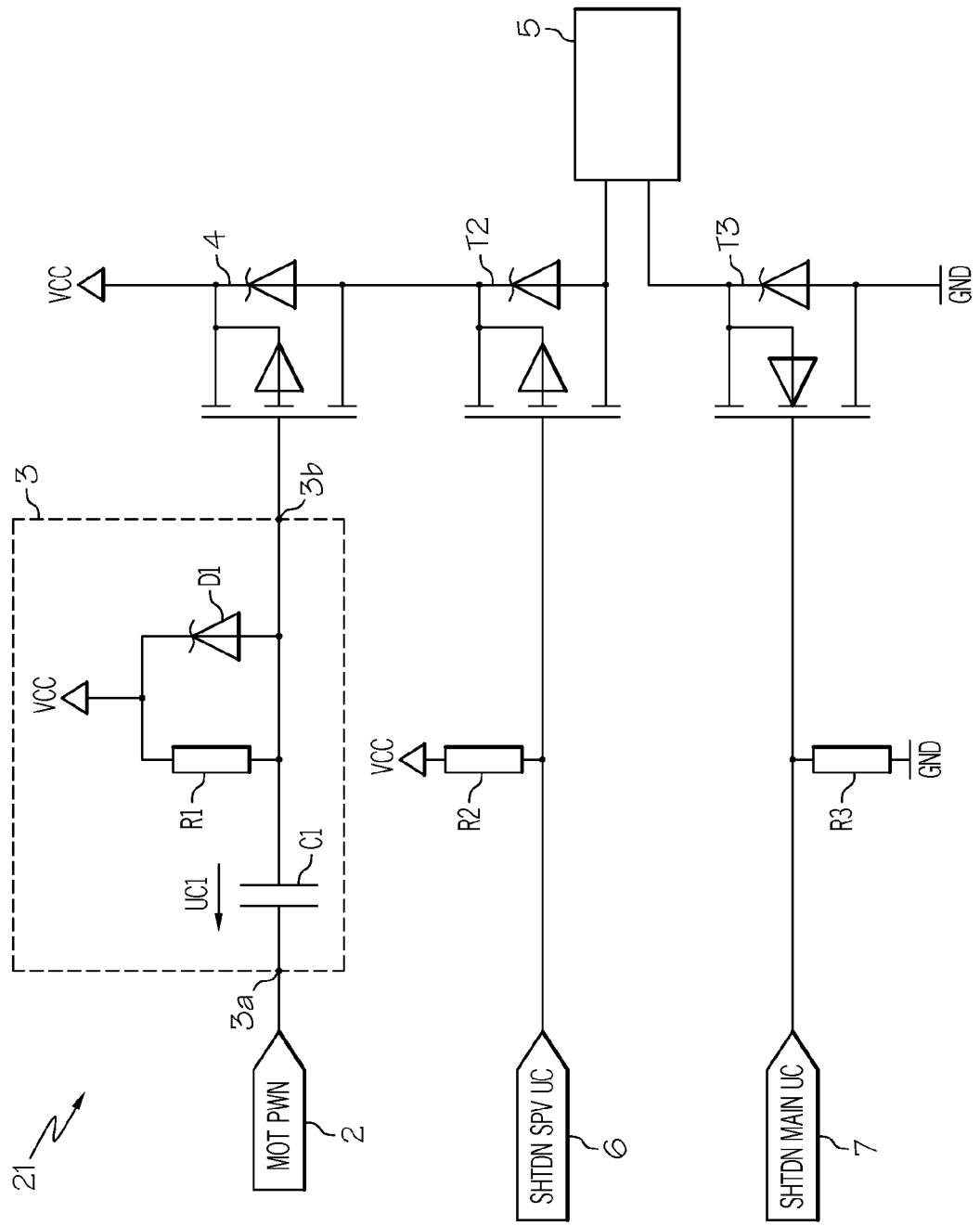
FIG. 3 shows the embodiment of FIG. 1 with two additional switches.

FIG. 3 shows a medical infusion system 21 with a signal generator 2, a safety circuit 3, a PMOSFET 4 and a pump motor 5 that is basically identical to the medical infusion system 1 shown in FIG. 1. In addition, there is a PMOSFET T2 in the power supply circuit between pump motor 5 and PMOSFET 4 and an NMOSFET T3 between the pump motor 5 and the ground pole of the power supply (not shown). The gate of PMOSFET T2 is directly connected to a signal generator 6 and to VCC via the pull-up resistor R2. The gate of NMOSFET T3 is directly connected to a signal generator 7 and to ground via pull-down resistor R3.

The functionality of medical infusion system 21 is basically identical to that of medical infusion system 1 according to FIG. 1. PMOSFET T2 and NMOSFET T3 are additional switches to interrupt the power supply circuit.

If signal generator 6 delivers a high signal, PMOSFET T2 interrupts the power supply circuit. If signal generator 6 delivers a low signal, PMOSFET T2 closes the power supply circuit. If signal generator 6 does not deliver any defined signal, for example, if the connection is interrupted, the potential at the gate of PMOSFET T2 is high via resistor R2 and the power supply circuit is interrupted.

The functionality of signal generator 7, resistor R3 and NMOSFET T3 is basically the same as of signal generator 6, resistor R2 and PMOSFET T2 with the difference that NMOSFET closes the power supply circuit if signal generator 7 delivers a high signal. NMOSFET T3 interrupts the power supply circuit if signal generator 7 delivers a low signal or no defined signal. In the latter case, resistor R3 pulls the potential at the gate of NMOSFET T3 down to ground potential.

In the medical infusion system 21, preferably the safety circuit 3, the PMOSFETs 4 and T2, the NMOSFET T3 and the pump motor 5 are encapsulated to a liquid-tight unit. This unit has only five electric ports, two for connecting the unit to a power supply and three for connecting the unit to the signal generator 2 and the signal generators 6 and 7. Optionally, the signal generator 2, too, can be included in the liquid-tight unit. Optionally, the signal generators 6 and 7, too, can be included in the liquid-tight unit.

Figure 4:
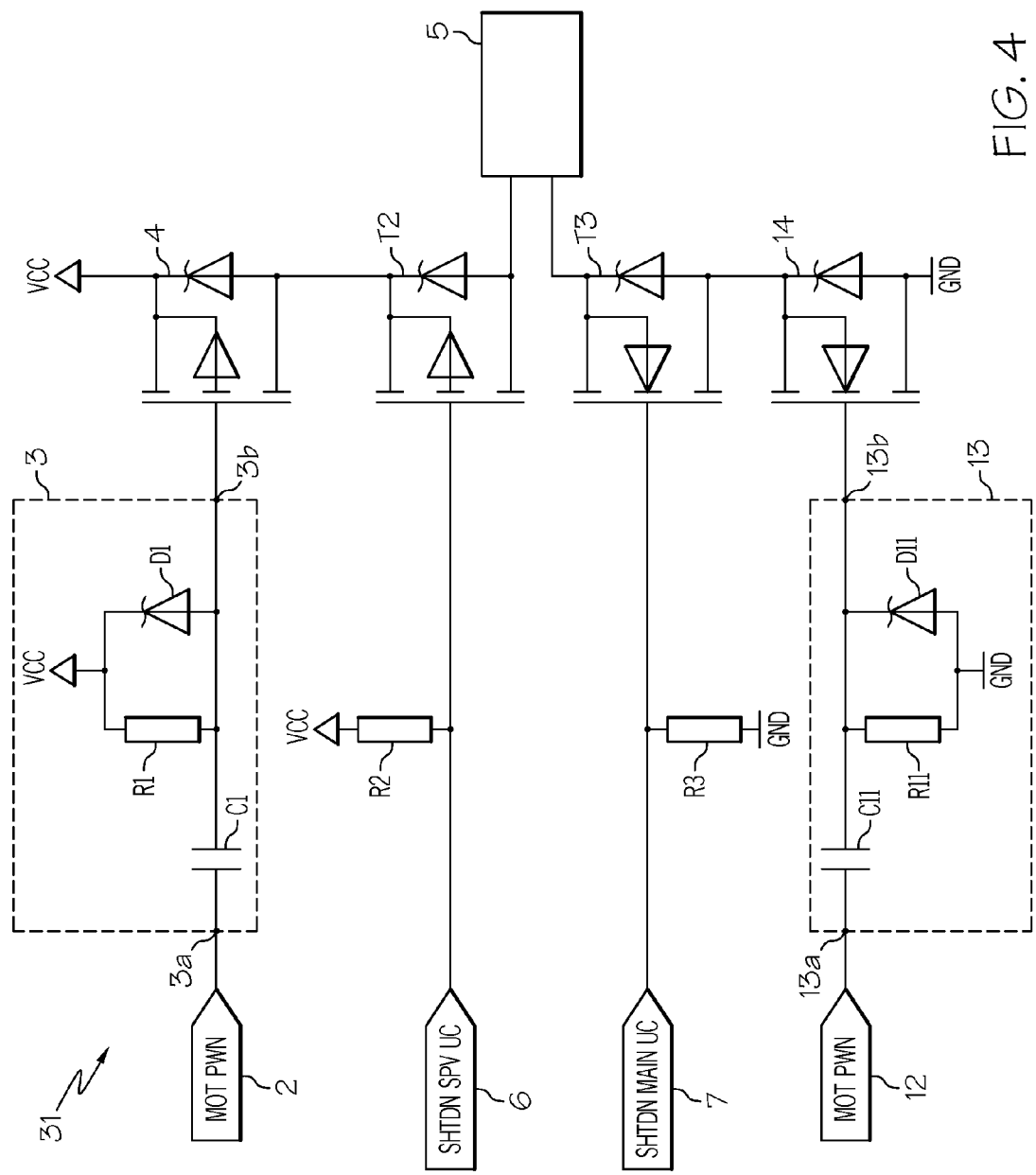
FIG. 4 shows another medical infusion system combining the embodiments according to FIGS. 2 and 3.

FIG. 4 shows a medical infusion system 31 combining the medical infusion systems 21 shown in FIGS. 3 and 11 shown in FIG. 2. The NMOSFET 14 is placed in the power supply circuit between the NMOSFET T3 and the ground pole of the power supply (not shown). There is only current flowing through pump motor 5 if all four switches i.e., FETs 4, 14, T2 and T3 are in conducting state. This is only the case if PWM signal generator 12 delivers a PWM signal that is the inverse of the PWM signal delivered by signal generator 2, signal generator 6 delivers a low signal and signal generator 7 delivers a high signal.

In the medical infusion system 31, preferably the safety circuits 3 and 13, the PMOSFETs 4 and T2, the NMOSFETs 14 and T3 and the pump motor 5 are encapsulated to a liquid-tight unit. This unit has only six electric ports, two for connecting the unit to a power supply and four for connecting the unit to the PWM signal generators 2 and 12 and the signal generators 6 and 7. Optionally, the PWM signal generators 2 and 12, too, can be included in the liquid-tight unit. Optionally, the whole electronic, too, can be included in the liquid-tight unit.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. As such, the embodiments described above are purely illustrative and not meant to limit the scope of the invention.

What is claimed is:

1. A medical infusion system comprising:
   a control signal generator;
   a safety circuit;
   a switching device; and
   a pump motor, wherein:
      the pump motor and the switching device are connected in series and constitute a power supply circuit to be connected to a power supply,
      the control signal generator is configured to generate a control signal having an "on" potential and an "off" potential present at a control input of the switching device, wherein the "on" potential is any potential which makes the switching device close the power supply circuit, and the "off" potential is any potential which makes the switching device open the power supply circuit,
      an output of the control signal generator is connected to an input of the safety circuit,
      an output of the safety circuit is connected to the control input of the switching device, and
      the safety circuit is configured to apply the "off" potential to its output if there is an "off" potential at its input, apply the "on" potential to its output if there continuously is an "on" potential at its input for a duration up to a predetermined amount of time, and apply the "off" potential to its output if there continuously is an "on" potential at its input for a duration longer than a predetermined amount of time.

2. The medical infusion system according to claim 1, wherein the control signal generator generates a PWM signal.

3. The medical infusion system according to claim 2, wherein the predetermined amount of time is longer than the cycle of the PWM signal.

4. The medical infusion system according to claim 2, wherein the predetermined amount of time is selected from 2, 5, 10 and 100 times the cycle of the PWM signal.

5. The medical infusion system according to claim 1, wherein the safety circuit, the switching device and the pump motor constitute a unit that is impervious to fluids.

6. The medical infusion system according to claim 1, wherein the safety circuit comprises an RC circuit.

7. The medical infusion system according to claim 6, wherein one pin of the capacitor of the RC circuit is directly connected to the input of the safety circuit, the other pin of the capacitor is directly connected to the output of the safety circuit, one pin of the resistor of the RC circuit is directly connected to the output of the safety circuit and the other pin of the resistor is connected to a constant potential being equal to the "off" potential.

8. The medical infusion system according to claim 6, further comprising a diode in parallel to a resistor of the RC circuit so that a capacitor of the RC circuit is discharged via the diode if the signal at the input of the safety circuit has "off" potential.

9. The medical infusion system according to claim 1, wherein the switching device is a PMOSFET, the "on" potential is ground (GND) and the "off" potential is a constant positive potential.

10. The medical infusion system according to claim 1, wherein the switching device is an NMOSFET, the "on" potential is a constant positive potential and the "off" potential ground (GND).

11. The medical infusion system according to claim 9, wherein the constant positive potential equals to the voltage of the power supply.

12. The medical infusion system according to claim 10, wherein the constant positive potential equals to the voltage of the power supply.

13. The medical infusion system according to claim 1, wherein the switching device is a mechanical switch.

14. The medical infusion system according to claim 1, wherein the switching device is a transistor.

15. A method for driving a pump motor in a medical infusion system, wherein the pump motor and a switching device constitute a power supply circuit to be connected to a power supply, the method comprising:
  receiving at a control input of the switching device a control signal from a control signal generator with a safety circuit, wherein the control signal includes an "on" potential and an "off" potential, wherein the "on" potential is any potential that makes the switching device close the power supply circuit, and the "off" potential is any potential that makes the switching device open the power supply circuit;
  switching the power supply circuit of the pump motor by the switching device according to the control signal applied to the control input of the switching device;
  applying the "off" potential to its output if there is the "off" potential at its input;
  applying the "on" potential to its output if there continuously is the "on" potential at its input for a duration up to a predetermined amount of time; and
  applying the "off" potential to its output if there continuously is the "on" potential at its input for a duration longer than a predetermined amount of time.

16. The method according to claim 15, wherein the received control signal is a PWM signal.

17. The method according to claim 15, wherein a capacitor of an RC circuit within the safety circuit is charged via a resistor of the RC circuit while the signal received by the safety circuit has the "on" potential and the potential at the pin of the capacitor that is connected to the resistor is applied to the control input of the switching device.

18. The method according to claim 17, wherein the capacitor is discharged by a diode in parallel to the resistor if the received signal has the "off" potential.

* * * * *

UNITED STATES PATENT AND TRADEMARK OFFICE
CERTIFICATE OF CORRECTION

PATENT NO. : 8,876,769 B2
APPLICATION NO. : 12/484335
DATED : November 4, 2014
INVENTOR(S) : Jean Noël Fehr et al.

It is certified that error appears in the above-identified patent and that said Letters Patent is hereby corrected as shown below:

In the Specification

Col. 1, Line 9,
"sion system with pulse width modulation and a safety circuit." should read
--sion system with pulse width modulation and a safety circuit--;

Col. 2, Line 30,
"wherein like numerals designate corresponding parts in a" should read
--wherein like numerals designate corresponding parts in--;

Col. 3, Line 51,
"to high or via versa." should read
--to high or vice versa.--;

Col. 3, Lines 64-65,
"drug to be infused to the user at a time can be limited to a none live –threatening dose. In a preferred embodiment, the prede-" should read
--drug to be infused to the user at a time can be limited to a non life–threatening dose. In a preferred embodiment, the prede- --; and Col. 8, Line 67,
"be $R1 = 22\ k\Omega$ and $C1 = 10\ \mu f$, resulting in $T = 1.1\ s$." should read
--be $R1 = 22\ k\Omega$ and $C1 = 10\ \mu F$, resulting in $T = 1.1\ s$.--.

Signed and Sealed this
Fifth Day of January, 2016

Michelle K. Lee
*Director of the United States Patent and Trademark Office*